(12) United States Patent
Azarbarzin et al.

(10) Patent No.: US 9,775,642 B2
(45) Date of Patent: Oct. 3, 2017

(54) DEVICES AND METHODS FOR AUTOMATED SURGERY

(75) Inventors: Kurt Azarbarzin, Fairfield, CT (US); Ralph Stearns, Bozrah, CT (US)

(73) Assignee: Conmed Corporation, Utica, NY (US)

( * ) Notice: Subject to any disclaimer, the term of this patent is extended or adjusted under 35 U.S.C. 154(b) by 1336 days.

(21) Appl. No.: 13/704,411

(22) PCT Filed: May 24, 2011

(86) PCT No.: PCT/US2011/037814
§ 371 (c)(1),
(2), (4) Date: Aug. 7, 2013

(87) PCT Pub. No.: WO2012/005819
PCT Pub. Date: Jan. 12, 2012

(65) Prior Publication Data
US 2014/0088491 A1    Mar. 27, 2014

Related U.S. Application Data

(60) Provisional application No. 61/347,714, filed on May 24, 2010.

(51) Int. Cl.
*A61B 17/34* (2006.01)
*A61B 17/00* (2006.01)
*A61B 34/30* (2016.01)
*A61B 90/00* (2016.01)

(52) U.S. Cl.
CPC .......... *A61B 17/3421* (2013.01); *A61B 34/30* (2016.02); *A61B 17/3423* (2013.01); *A61B 17/3462* (2013.01); *A61B 17/3474* (2013.01); *A61B 2017/00544* (2013.01);
(Continued)

(58) Field of Classification Search
CPC ............... A61B 17/3421; A61B 34/30; A61B 2090/064; A61B 2034/302; A61B 17/3462; A61B 17/3474; A61B 2017/00544; A61B 2017/3445; A61B 17/3423
USPC ...... 604/26, 164.01–164.11, 167.01, 167.02, 604/264
See application file for complete search history.

(56) References Cited

U.S. PATENT DOCUMENTS 5,025,778 A * 6/1991 Silverstein ........... A61B 1/0008
600/104
5,141,498 A * 8/1992 Christian .............. A61M 39/06
251/149.1

(Continued)

*Primary Examiner* — Manuel Mendez
(74) *Attorney, Agent, or Firm* — Locke Lord LLP; Scott D. Wofsy; Arpita G. Buesing

(57) ABSTRACT

The disclosure includes systems and methods for performing surgery. In a first aspect, the system includes a trocar having in a nested configuration, an outer cannula, an inner cannula disposed within the outer cannula, the inner cannula defining the central longitudinal lumen at least in part to provide access through the trocar, a tube center component disposed within the outer cannula, and a ring jet assembly disposed within the outer cannula. In a further aspect, the system includes an instrument guide disposed in the central longitudinal lumen of the trocar. The instrument guide has a proximal end, a distal end, and a plurality of channels defined through the instrument guide from the proximal end to the distal end, each channel being adapted and configured to receive a surgical instrument.

20 Claims, 18 Drawing Sheets

(52) U.S. Cl.
CPC . *A61B 2017/3445* (2013.01); *A61B 2034/302* (2016.02); *A61B 2090/064* (2016.02)

(56) References Cited

U.S. PATENT DOCUMENTS

| | | | | |
|---|---|---|---|---|
| 5,197,955 | A * | 3/1993 | Stephens et al. | A61B 17/3462 604/167.01 |
| 5,312,391 | A * | 5/1994 | Wilk | A61B 17/00234 604/264 |
| 5,395,367 | A * | 3/1995 | Wilk | A61B 17/00234 606/1 |
| 5,454,365 | A * | 10/1995 | Bonutti | A61B 17/0218 600/204 |
| 5,720,730 | A * | 2/1998 | Blake, III | A61B 17/3498 604/167.02 |
| 5,746,720 | A * | 5/1998 | Stouder, Jr. | A61B 17/3417 604/117 |
| 6,277,064 | B1 * | 8/2001 | Yoon | A61B 1/00177 600/104 |
| 6,508,827 | B1 * | 1/2003 | Manhes | A61B 17/29 600/104 |
| 6,656,205 | B1 * | 12/2003 | Manhes | A61B 17/29 606/205 |
| 7,850,600 | B1 * | 12/2010 | Piskun | A61B 1/05 600/114 |
| 7,854,724 | B2 * | 12/2010 | Stearns | A61B 17/3421 604/164.01 |
| 8,518,024 | B2 * | 8/2013 | Williams | A61B 1/00052 606/1 |
| 8,690,831 | B2 * | 4/2014 | Duke | A61B 17/3421 604/164.01 |
| 2010/0114032 | A1 * | 5/2010 | Widenhouse | A61B 17/3421 604/167.03 |

* cited by examiner

Fig. 25
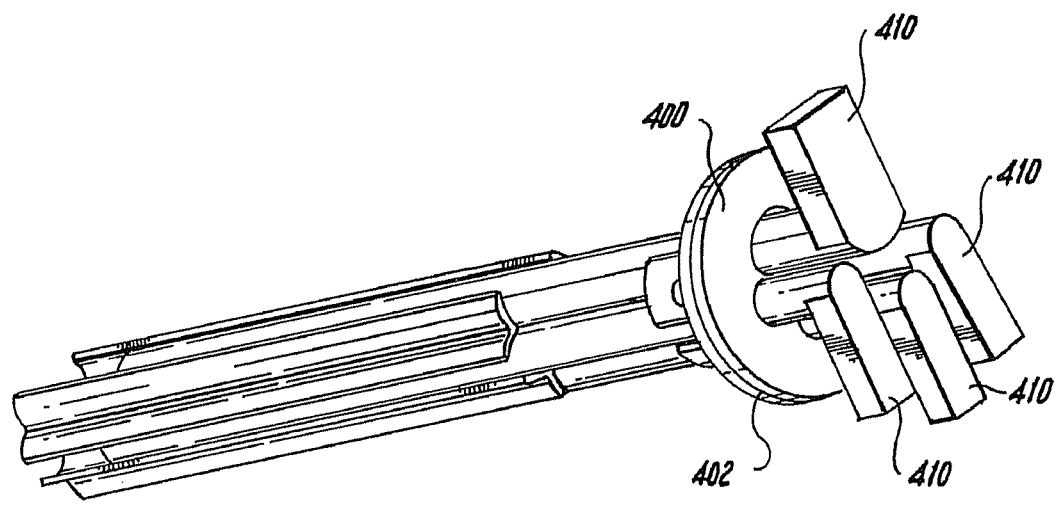
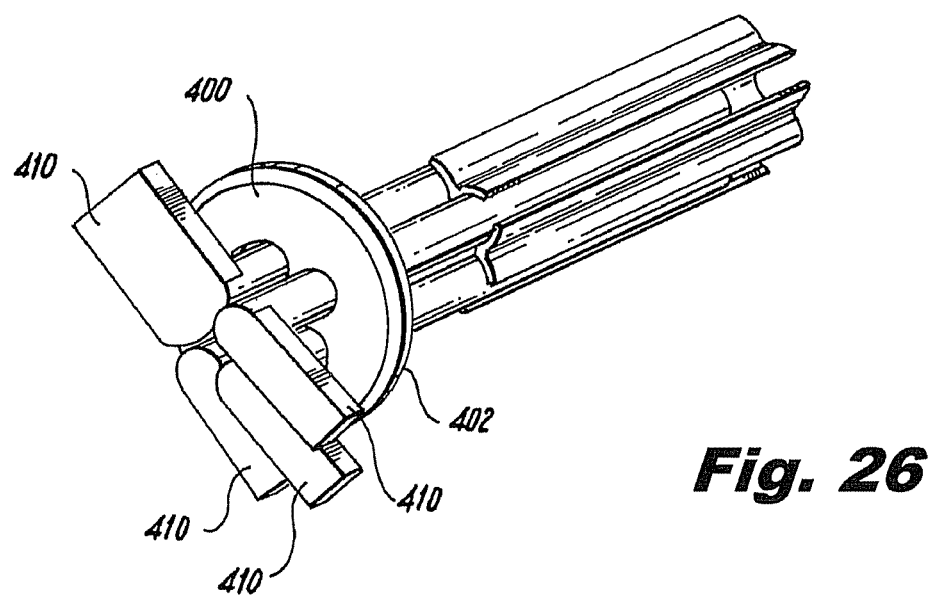
Fig. 26

DEVICES AND METHODS FOR AUTOMATED SURGERY

CROSS-REFERENCE TO RELATED APPLICATIONS

This patent application is related to and claims the benefit or priority to U.S. Provisional Patent Application Ser. No. 61/347,714, filed May 24, 2010. This patent application is also related to U.S. patent application Ser. No. 12/577,179, filed Oct. 10, 2009, U.S. patent application Ser. No. 12/577,189, filed Oct. 11, 2009, U.S. patent application Ser. No. 12/587,584, filed Oct. 9, 2009, U.S. Provisional Patent Application Ser. No. 61/250,521, filed Oct. 11, 2009, U.S. patent application Ser. No. 11/786,832, filed Apr. 13, 2007, U.S. patent application Ser. No. 11/544,856, filed Oct. 6, 2006 and U.S. Patent Application Ser. No. 61/104,501, filed Oct. 10, 2008. Each of the aforementioned patent applications is incorporated by reference herein in its entirety.

BACKGROUND

1. Field of the Disclosure

The present disclosure relates to surgical access devices (or surgical access ports) and related methods. More particularly, the present invention relates to such devices that are advantageously adapted for use in single-incision laparoscopic surgical ("SILS") procedures that use automated means for performing the surgery, such as robotic means controlled by an operator. The present disclosure also relates to kits and methods involving such surgical access devices.

2. Description of the Related Art

Increasingly, techniques are being developed for performing minimally invasive surgical procedures with a single incision, in order to reduce trauma and reduce the amount of scarring of a patient. It is often difficult to insert multiple traditional surgical instruments simultaneously through a single incision, due to mutual interference, and lack of available space. It has therefore become necessary to develop devices, systems and procedures to facilitate such approaches. In parallel with the foregoing, many advances have been made in the field of remote surgery that relies on robotics. The present invention provides improvements in the field of SILS, particularly as it relates to robotic techniques, as set forth below.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

To achieve these and other advantages and in accordance with the purpose of the disclosure, as embodied herein, the disclosure includes a system for use in a surgical procedure. In a first aspect, the system includes a trocar having a substantially tubular inner wall and a substantially tubular outer wall, the trocar having a proximal end and a distal end, the inner wall defining a central longitudinal lumen to provide access through the trocar. The trocar includes, in a nested configuration, an outer cannula, an inner cannula disposed within the outer cannula, the inner cannula defining the central longitudinal lumen at least in part to provide access through the trocar, a tube center component disposed within the outer cannula, and a ring jet assembly disposed within the outer cannula. The tube center component and ring jet assembly interfit to define a plurality of nozzle passages disposed annularly about a central longitudinal axis defined by the trocar. The tube center component and ring jet assembly are adapted and configured to define a plenum capable of receiving a pressurized gas, the plenum being in fluid communication with the nozzle passages. The nozzle passages, in turn, are adapted and configured to issue high speed jets substantially parallel to a longitudinal axis of the trocar toward the distal end of the trocar.

In a further aspect, the system includes an instrument guide disposed in the central longitudinal lumen of the trocar. The instrument guide has a proximal end, a distal end, and a plurality of channels defined through the instrument guide from the proximal end to the distal end, each channel being adapted and configured to receive a surgical instrument.

In accordance with one embodiment, the instrument guide includes a radially-enlarged flared proximal region and an elongate distal region, wherein each channel is defined by at least one elongate curved wall that is angled away from the central longitudinal axis of the trocar when the instrument guide is inserted into the trocar. Preferably, at least one of the channels of the instrument guide is open along its length along a side of the instrument guide. In a further embodiment, at least one of the channels of the instrument guide has a generally round cross-section along its length. In another embodiment, at least one of the channels of the instrument guide has a generally elliptical cross-section along its length.

In accordance with a further aspect, the trocar further can include a fluid manifold attached to an exterior portion of the outer cannula, wherein the manifold defines a plurality of fluid passages therethrough. One of the passages of the fluid manifold is preferably in direct fluid communication with the plenum that is in fluid communication with the nozzle passages. In a further embodiment, the trocar can further include a suction extension disposed within the outer cannula located distally with respect to the nozzle passages.

In accordance with a further aspect, the trocar can further include a sound baffle within the outer cannula located proximally with respect to the nozzle passages, wherein the sound baffle is made from a compliant material. The sound baffle includes a proximal peripheral bead a distal peripheral bead, a hollow body bounded by the proximal peripheral bead and the distal peripheral bead defined by an irregular surface, wherein the hollow body is adapted and configured to deflect to permit at least one surgical instrument to pass therethrough. The hollow body can include a proximal peripheral portion connected to distal peripheral portion by way of a neck region. The neck region can include an undulation therein for baffling sound emanating from flow through the nozzle passages. The proximal peripheral bead and the distal peripheral bead can be captured and held in place between adjacent portions of the trocar.

In accordance with a further aspect, the trocar can define a side port therethrough from an outer surface of the outer cannula through the inner cannula into the central longitudinal lumen. The side port is preferably angled with respect to the central longitudinal axis. The side port is adapted and configured to receive an instrument therethrough and into the central longitudinal lumen.

The disclosure also provides a robotic surgical system. The system includes, in a first aspect, a remotely controlled surgical system having a plurality of remotely controllable arms, each arm being suitable for performing a portion of a surgical procedure, each arm being remotely controllable from a user console. The system further includes a trocar as described above, and an instrument guide, wherein each channel of the instrument guide is adapted and configured to receive one of the remotely controllable arms of the remotely controlled surgical system.

In further accordance with the disclosure, a method is provided of performing surgery on a patient. The method includes providing a remotely controlled surgical system having a plurality of remotely controllable arms, each arm being suitable for performing a portion of a surgical procedure, each arm being remotely controllable from a user console. The method further includes disposing a trocar as described above through an incision in a patient to access an interior portion of the patient. The method still further includes the step of disposing an instrument guide as described above in the central longitudinal lumen of the trocar, actuating the plurality of jets in the trocar by pressurizing the plenum of the trocar, disposing at least one remotely controllable arm through at least one of the instrument guides into the patient, and performing a surgical procedure using the at least one remotely controllable arm.

In accordance with a further aspect, the method can also include introducing an instrument through a side port defined through the trocar into the central longitudinal lumen, the side port being angled with respect to the central longitudinal axis. The instrument introduced through the side port can be selected from the group including a needle for delivering an agent into the patient, a retractor, a dilator, a grasper, a suction device and an irrigation device.

The disclosure further provides an instrument guide as described above for use with an automated/robotic surgical system, or in association with manual surgical techniques, preferably in association with the trocar described above.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the method and system of the disclosed embodiments. Together with the description, the drawings serve to explain principles of the disclosed embodiments.

BRIEF DESCRIPTION OF THE DRAWINGS

FIGS. 25-28 are various views of a second representative embodiment of an instrument guide in accordance with the disclosed embodiments that may include one or more inserts.

DETAILED DESCRIPTION

Figure 1:
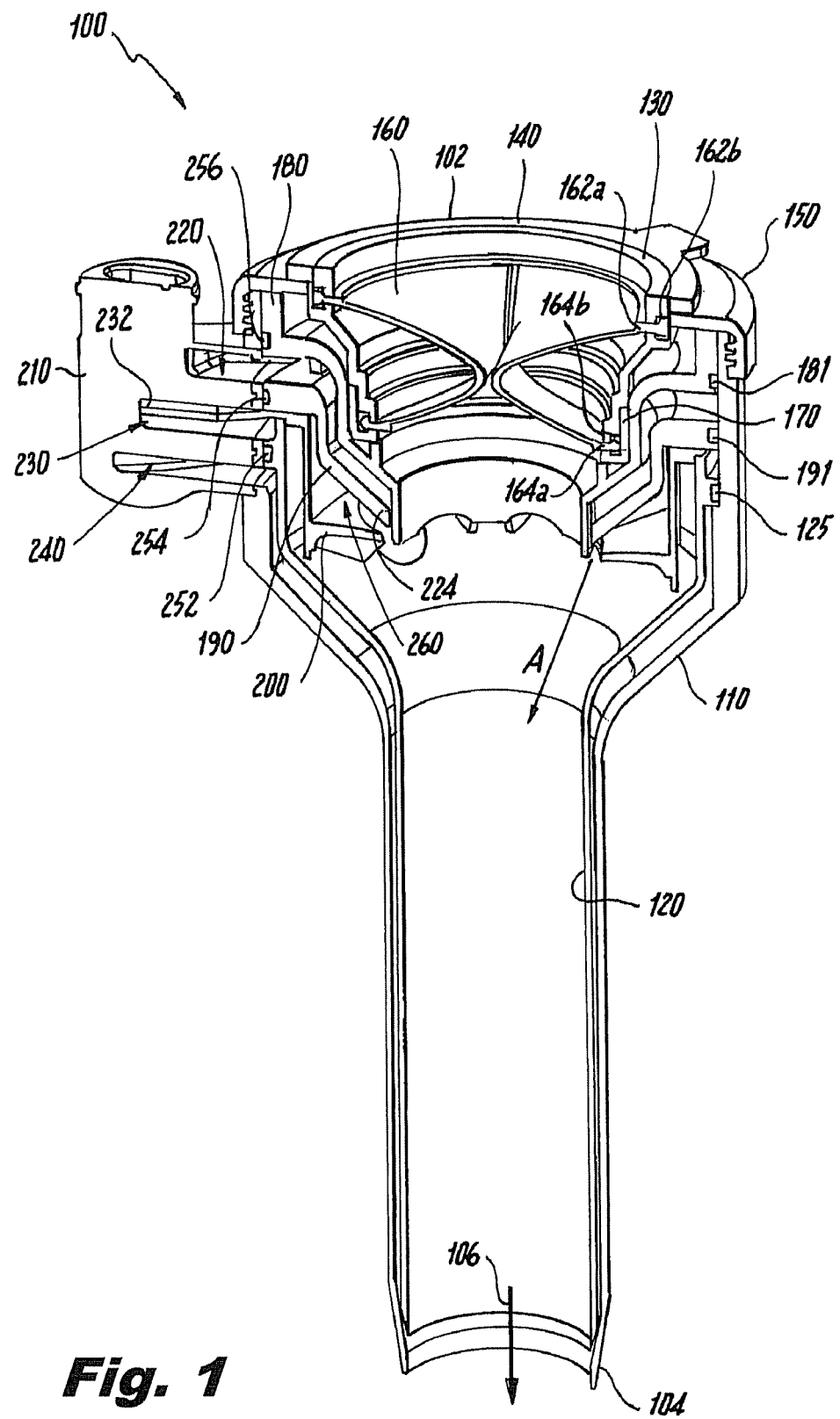
FIG. 1 is an isometric cut-away view of a portion of a first representative embodiment of a trocar in accordance with the disclosed embodiments.
Figure 2:
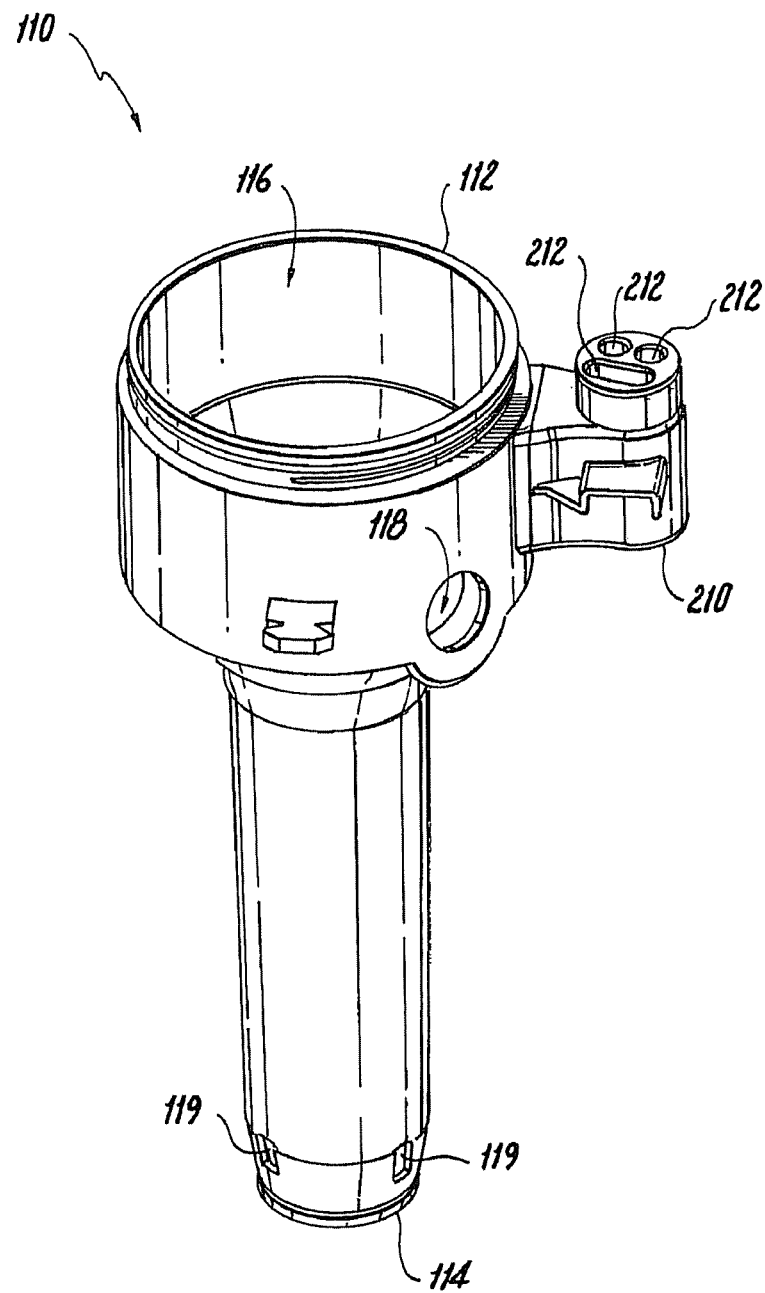
FIG. 2 is an isometric view of a portion of the trocar of FIG. 1 in accordance with the disclosed embodiments.
Figure 3:
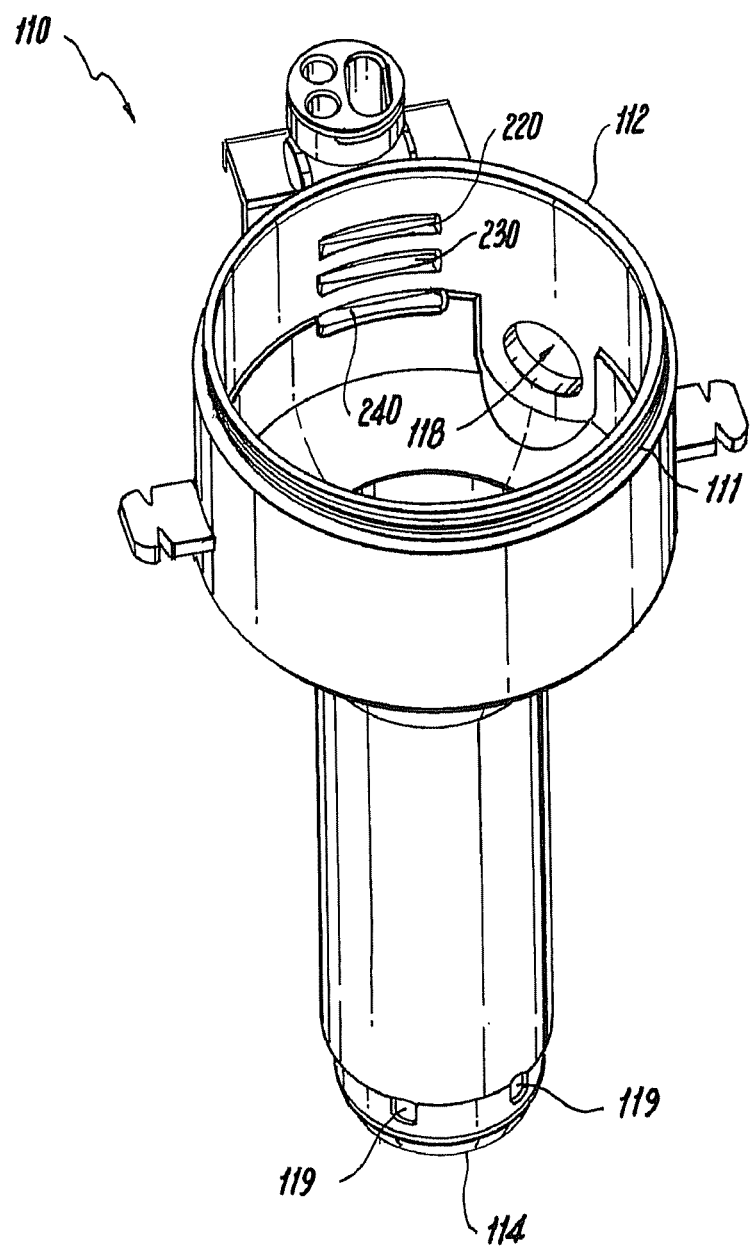
FIG. 3 is a further isometric view of the portion of the trocar of FIG. 1 illustrated in FIG. 2.
Figure 4:
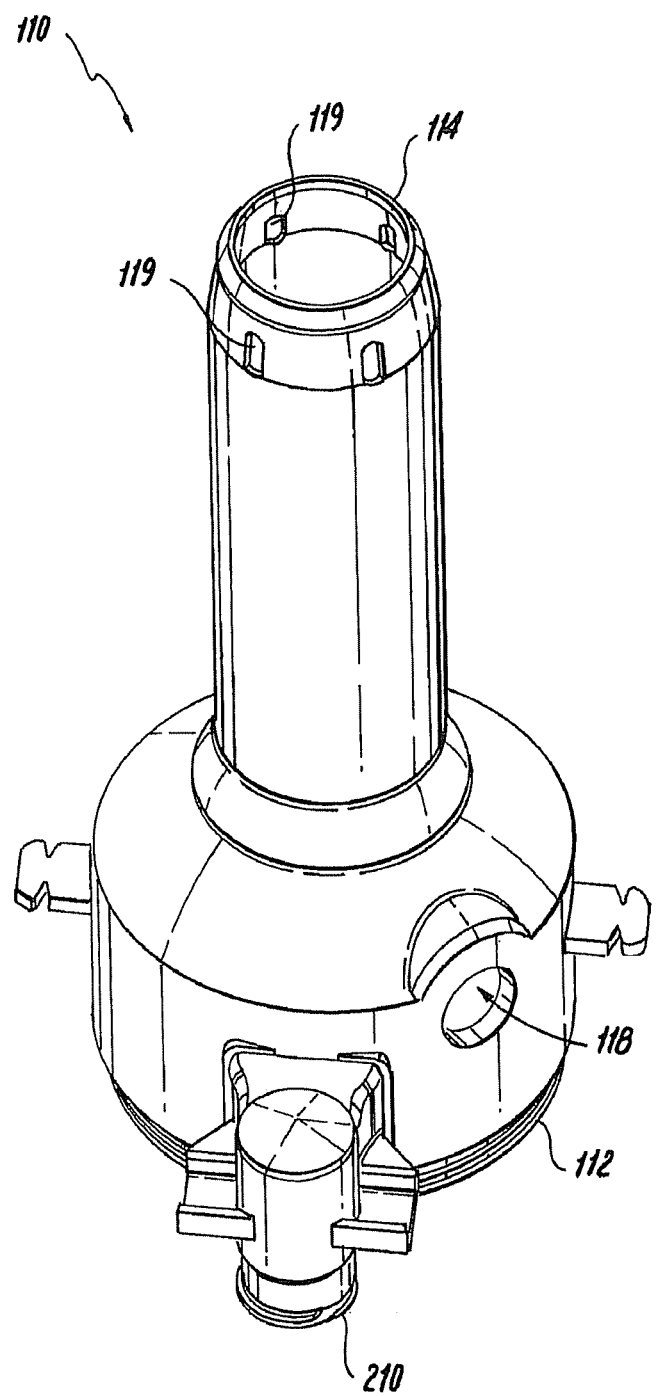
FIG. 4 is still a further isometric view of the portion of the trocar of FIG. 1 illustrated in FIG. 2, illustrating the device as viewed from the distal end thereof.
Figure 5:
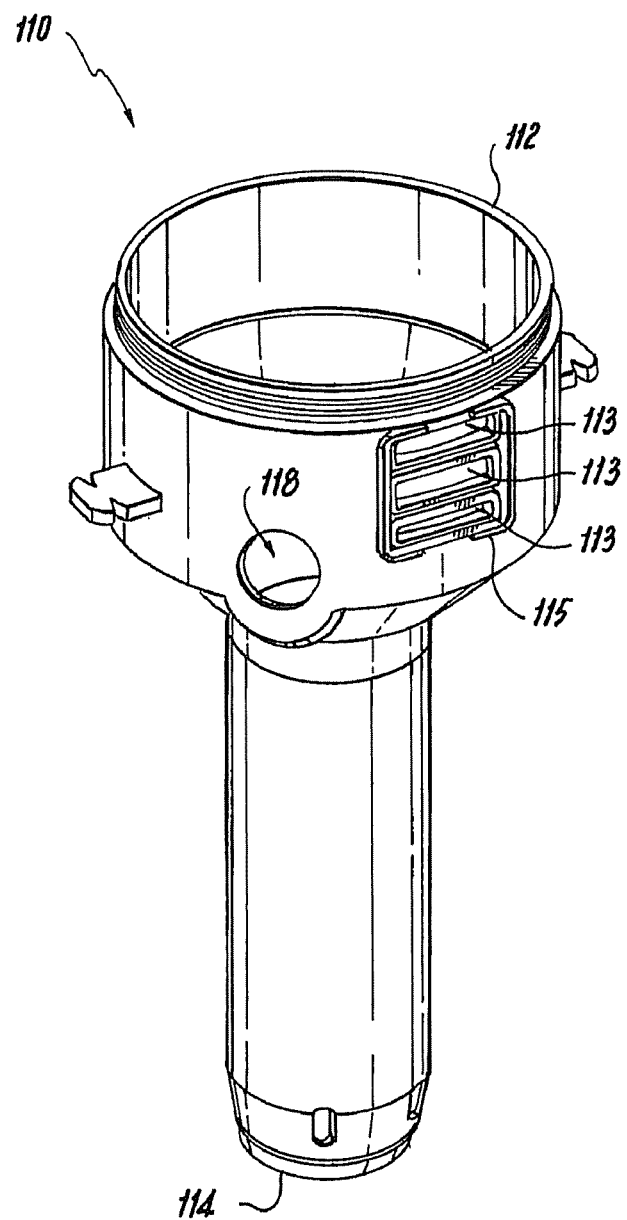
FIG. 5 is an isometric view of a portion of the trocar of FIG. 1 in accordance with the disclosed embodiments.

Reference will now be made in detail to the present preferred embodiments of the disclosure, examples of which are illustrated in the accompanying drawings. The methods and corresponding steps of the disclosed embodiments will be described in conjunction with the detailed description of the systems. The accompanying drawings, which are incorporated in and constitute part of this specification, are included to illustrate and provide a further understanding of the method and system of the disclosure. Together with the description, the drawings serve to explain the principles of the disclosed embodiments.

Robotic surgery systems have gained acceptance in the field and have become a preference for certain patients and surgeons. One such system is generally known as the DaVinci surgical system from Intuitive Surgical, Inc. (Sunnyvale, Calif., USA). Aspects of this system can be found in U.S. Pat. Nos. 7,695,481, 7,316,681, 7,453,227, 7,666,191, 7,507,199 and 7,689,320, among others. Each of the aforementioned patents is incorporated by reference herein in its entirety.

A central aspect of the DaVinci system is the use of multiple robotic arms and instruments that are controlled remotely from a user console. Each of the robotic arms may include a different surgical instrument as an end effector thereon, such as a clamp, forceps, scalpel and the like. Another central aspect of such a system is that remote visualization (such as by using an endoscope) is used to view the area inside the patient being operated on. A disadvantage with the DaVinci system is that multiple abdominal openings or incisions are generally used to accommodate each of the instruments that is to be inserted into the patient.

It is typically desirable to use as few abdominal openings as possible within a patient so as to speed recovery. In the case of laparoscopic surgery, it is particularly difficult to use a single trocar with a large opening to accommodate a plurality of instruments, as mechanical trocar seals generally known in the art work best when accommodating a single instrument to prevent the loss of insufflation gas through the trocar, as well as to prevent the escape of bodily fluids through the trocar. Specifically, use of an instrument that does not have a round cross section, or use of multiple instruments through a single trocar is disfavored because it results in poor mechanical sealing around the periphery of the instrument.

However, Applicants have developed a series of trocars that do not use typical mechanical seals to maintain a pressure differential between the operating room and an insufflated abdominal cavity. These trocars generally depend instead on the momentum of a high speed gas stream to counteract gas attempting to escape from the abdomen. Examples of such trocars can be found in the patent applications incorporated by reference on the first page of this patent application as well as those disclosed in U.S. Pat. No. 7,182,752, U.S. Pat. No. 7,285,112, U.S. Pat. No. 7,338,473 and U.S. Pat. No. 7,413,559, which are also incorporated by reference herein in their entireties. Such trocars do not use a mechanical seal to prevent the escape of insufflation gas or body fluids or effluents from the insufflated abdominal cavity of a patient. As a result, multiple surgical instruments of differing cross sections can be used alone, or simultaneously, to perform any number of procedures.

As a result of this advantage, it is possible to use such a trocar in cooperation with a robotic system such as the DaVinci system described above to perform a surgical procedure, such as a laparoscopic procedure, using multiple robotic instruments and a visualization scope through a single trocar. To facilitate such a procedure, a trocar and various inserts are provided herein to guide multiple robotic surgical instruments.

By way of introduction, an exemplary trocar is provided and illustrated in FIGS. 1-18. As embodied herein and as illustrated in FIG. 1, trocar 100 includes a proximal end 102, a distal end 104 and a substantially cylindrical bore 106 therethrough from the proximal end 102 to the distal end 104. Bore 106 is preferably sized and adapted to receive an instrument insert and instruments, described in detail below with respect to FIGS. 19-28.

As further illustrated in FIG. 1, trocar 100 is made by assembling a number of nested components discussed in further detail below. As depicted in FIG. 1, trocar 100 includes, in a nested configuration, an outer cannula 110, an inner cannula 120, a cap spacer ring 130, a stepped conical spacer 140, an upper cap 150, a sound baffle 160, a bottom cap 170, a tube center component 180, a ring jet assembly 190 and a suction extension 200. Cannula 210 further includes a fluid manifold 210 attached to an exterior portion of the outer cannula 110. Each of the aforementioned components will now be illustrated in further detail.

Various views of outer cannula 110 are depicted in FIGS. 2-5. As illustrated, outer cannula 110 has a proximal end 112, a distal end 114, and defines a longitudinal bore 116 therethrough. As further illustrated, outer cannula 110 also defines a side port 118 therein (that aligns with port 128 of inner cannula 120) to receive an instrument therethrough and into the bore 106 of trocar 100. Such instruments can include, for example, needles and the like for delivering various agents into the abdominal cavity or locally to tissues or organs within the abdominal cavity of a patient, retractors, dilators, graspers and suction and irrigation devices. The external surface of outer cannula 110 defines thereon a mounting fixture 115 to receive a fluid manifold 210. As illustrated, fluid manifold 210 defines therethrough three fluid passages that initiate at ports 212 on the top of manifold 210 and that terminate at slots 113 defined through the side of outer cannula 110. Each of the aforementioned fluid passages cooperate with the other portions of trocar 110 to define fluid passages, or plena. Each plenum, annotated by reference numerals 220, 230 and 240, serves a different purpose in operation of trocar 100 as described below. Manifold 210 is preferably permanently joined to outer cannula 110 to ensure that the fluid plena remain fluidly separated from each other by way of a gas tight seal. Outer cannula further defines a plurality of sensing ports 119 therethrough. When assembled with other trocar components, sensing ports 119 are in fluid communication with a sensing plenum 240 defined by, inter alia, outer cannula 110 and inner cannula 120.

Figure 6:
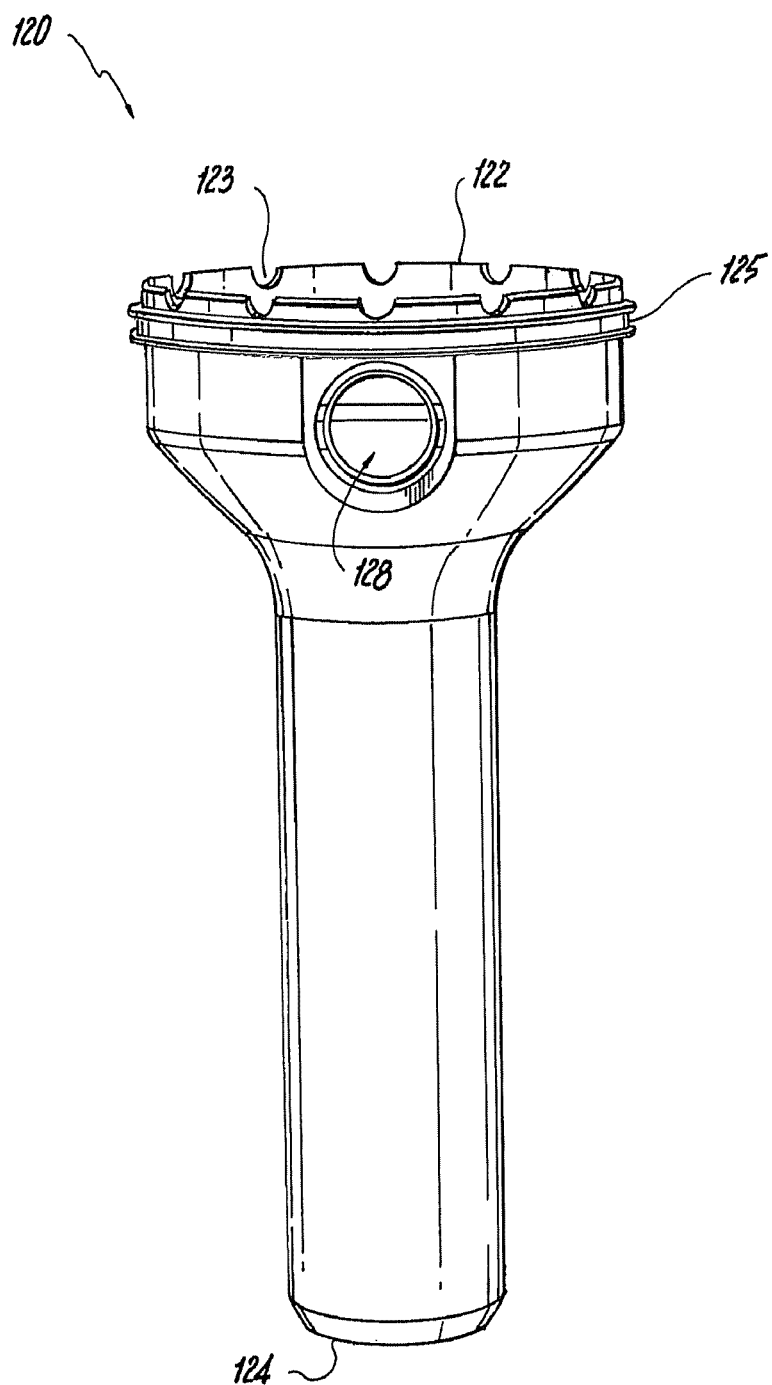
FIGS. 6-7 are views of an inner component of the trocar of FIG. 1 in accordance with the disclosed embodiments.
Figure 7:
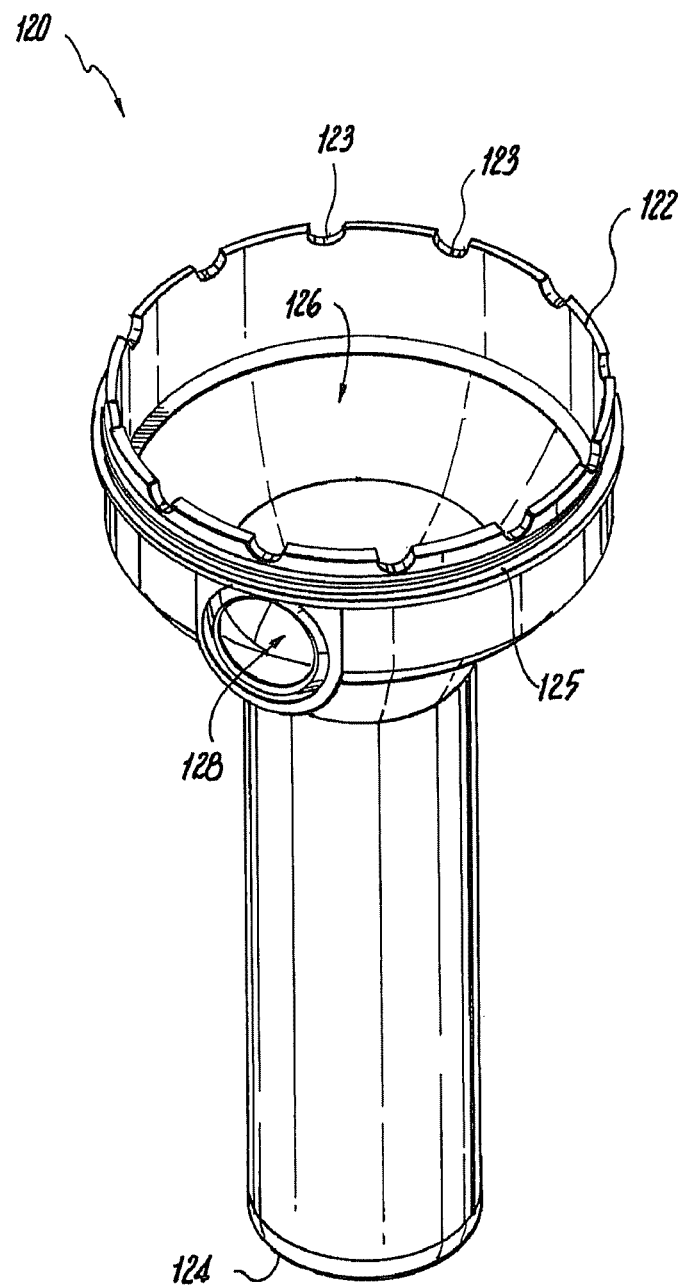

As illustrated in FIGS. 6-7, inner cannula 120 includes a proximal end 122, a distal end 124, and defines a longitudinal bore 126 therethrough. Port 128 aligns with port 118 to define a channel through which various auxiliary instruments can be introduced, such as needles, retractors, irrigation and suction instruments, and the like on an as-needed basis during a medical procedure. Inner cannula 120 defines a peripheral groove 125 about the proximal end 112 thereof that is adapted and configured to receive a sealing ring 252 (see FIG. 1). When assembled, sealing ring 252 is interposed between outer cannula 110 and inner cannula 120, thereby defining sensing plenum 240 in cooperation with dedicated passageway 242 in manifold 210.

Inner cannula 120 further defines a series of arcuate notches 123 along the upper periphery thereof. The periphery of proximal end 122 of inner cannula 120 seats in and is received by peripheral groove 203 defined in proximal end 202 of suction extension 200. When assembled, notches 123 act as fluid ports in fluid communication with passage 232 to define an exhaust or recirculation plenum 230, described in further detail below, for evacuating gas and other fluids from trocar 100 and/or the abdomen of the patient into a filtration and recirculation assembly (not shown).

Figure 12:
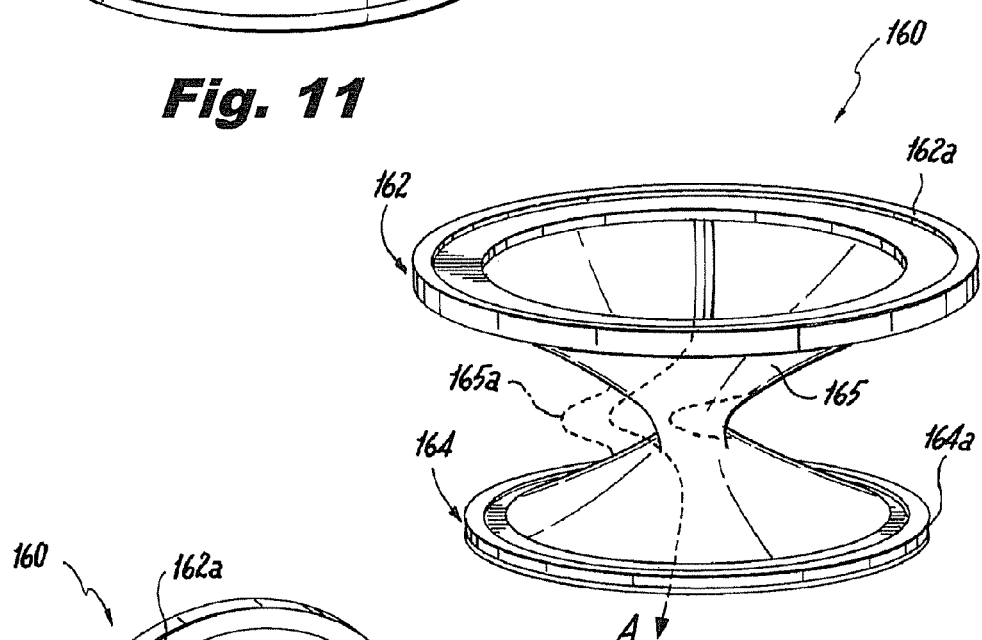
FIGS. 12-13 are isometric views of a sound baffle of the trocar of FIG. 1 in accordance with the disclosed embodiments.
Figure 13:
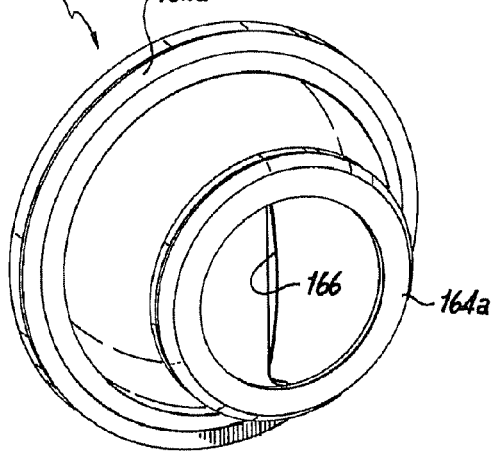

As illustrated in FIGS. 12-13, sound baffle 160 is flexible and is made from a compliant material, such as a resilient silicone-based polymeric material that is bio-acceptable that can regain its original shape after being deformed, such as by placing an instrument through bore 106 of trocar 100. Sound baffle 160 is depicted having an hourglass cross section (FIG. 1) and having a proximal peripheral portion 162 and a distal peripheral portion 164. As depicted, proximal peripheral portion 162 is connected to distal peripheral portion 164 by way of a neck region 165. By way of an alternative embodiment, neck region 165 can include an undulation, or fold, therein (illustrated in dashed lines as 165a). It has been found that such an undulation can further reduce the noise produced by trocar 100 in use. Moreover, while a passage 166 with a straight cross section has been illustrated, any desired shape for the cross-section can be used, such as a sinusoidal shape, as described in detail in U.S. Patent Application Ser. No. 61/250,521 (see, e.g., FIGS. 54-55 and related text). Sound baffle further defines a proximal peripheral bead 162a and a distal peripheral bead 164a.

Figure 8:
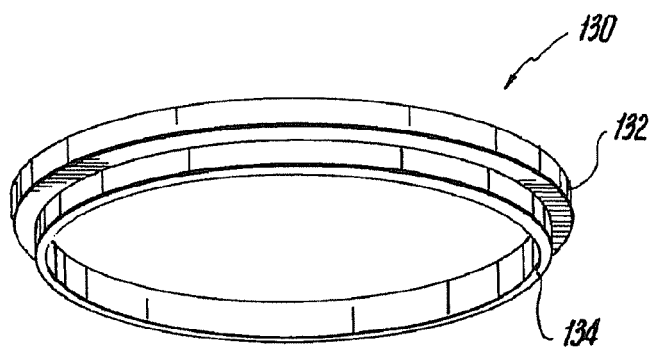
FIG. 8 is an isometric view of a cap spacer ring of the trocar of FIG. 1 in accordance with the disclosed embodiments.
Figure 9:
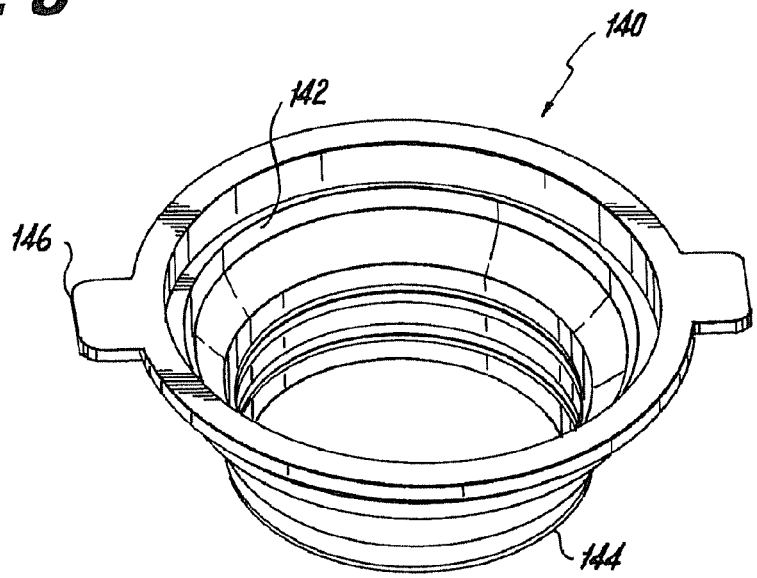
FIG. 9 is an isometric view of a stepped conical spacer of the trocar of FIG. 1 in accordance with the disclosed embodiments.
Figure 10:
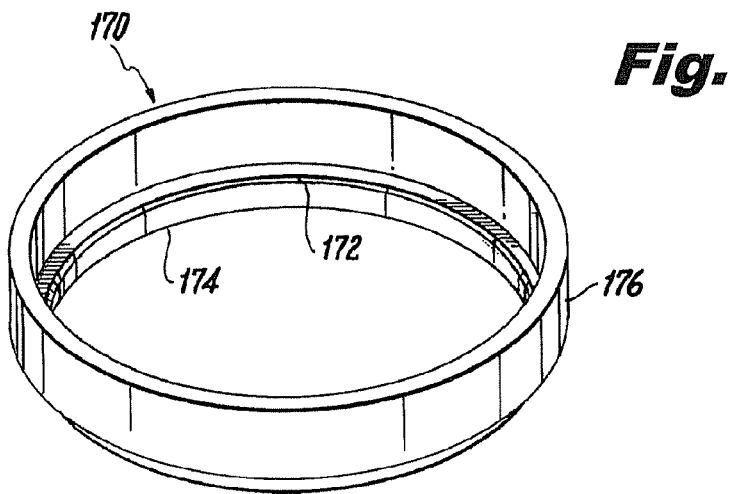
FIG. 10 is an isometric view of a bottom cap of the trocar of FIG. 1 in accordance with the disclosed embodiments.
Figure 11:
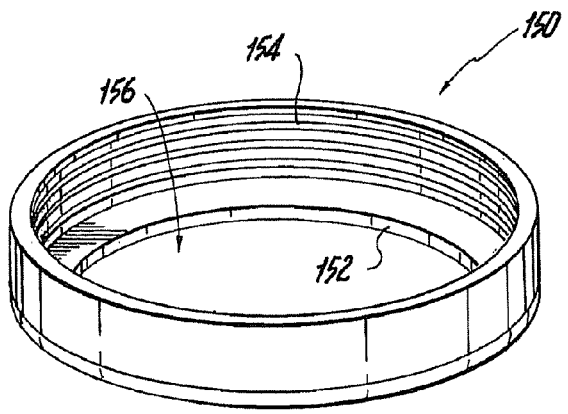
FIG. 11 is an isometric view of an upper cap of the trocar of FIG. 1 in accordance with the disclosed embodiments.

Sound baffle 160 is held in place by the combined sub-assembly of cap spacer ring 130, stepped conical spacer 140 and bottom cap 170. Specifically, and as illustrated in FIG. 8, cap spacer ring 130 includes a generally toroidal body defining an outer peripheral edge 132 and a distal engagement face 134 thereon. As further illustrated in FIG. 9, stepped conical spacer 140 defines an annular proximal engagement surface 142 and an annular distal engagement surface 144 thereon. As illustrated in FIG. 10, bottom cap 170 defines a proximal annular engagement surface 172, a distal annular engagement surface 174, and an outer peripheral face 176. With further reference to FIG. 1, the periphery of proximal portion 162 of baffle 160 is held in place between distal engagement surface 134 of cap spacer ring 130 and proximal engagement surface 142 of stepped conical spacer 140.

Figure 14:
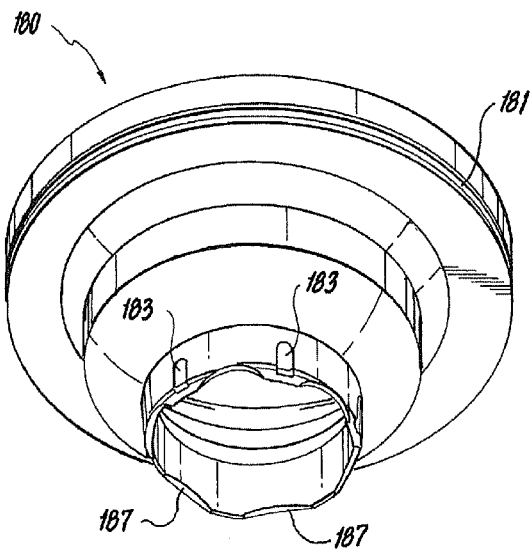
FIGS. 14-15 are isometric views of a tube center component of the trocar of FIG. 1 in accordance with the disclosed embodiments.
Figure 15:
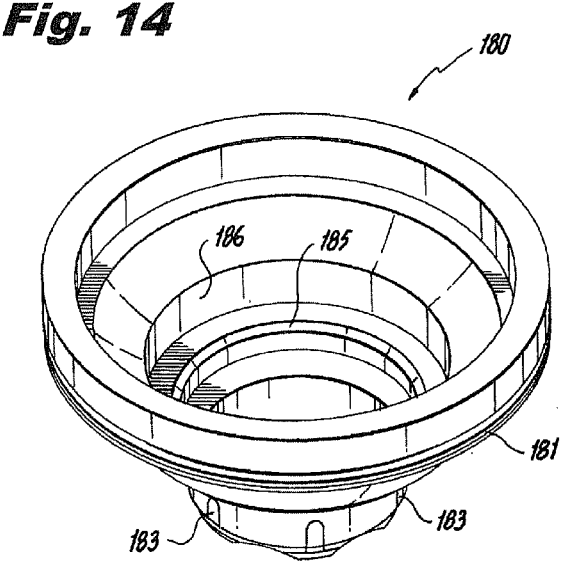
Figure 16:
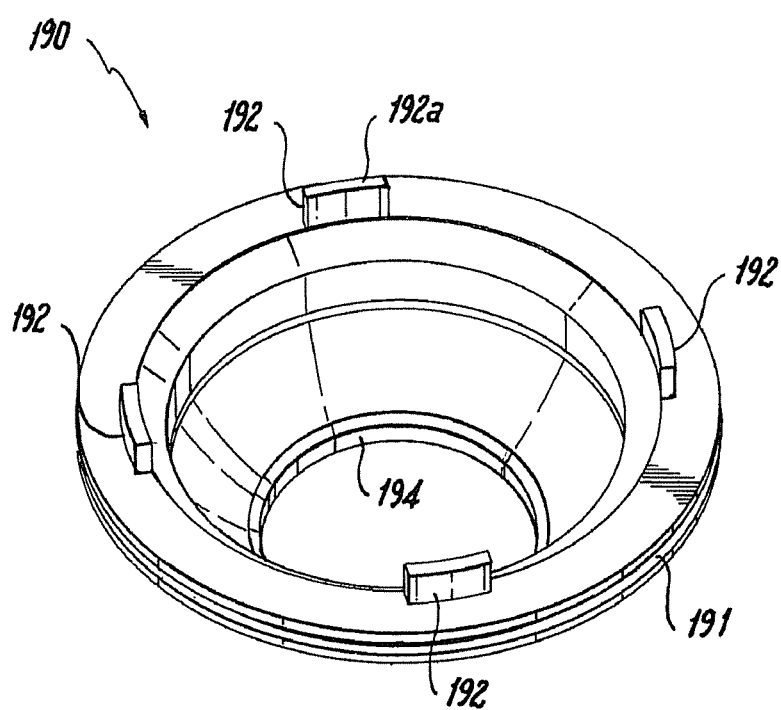
FIG. 16 is an isometric view of a ring jet assembly of the trocar of FIG. 1 in accordance with the disclosed embodiments.
Figure 17:
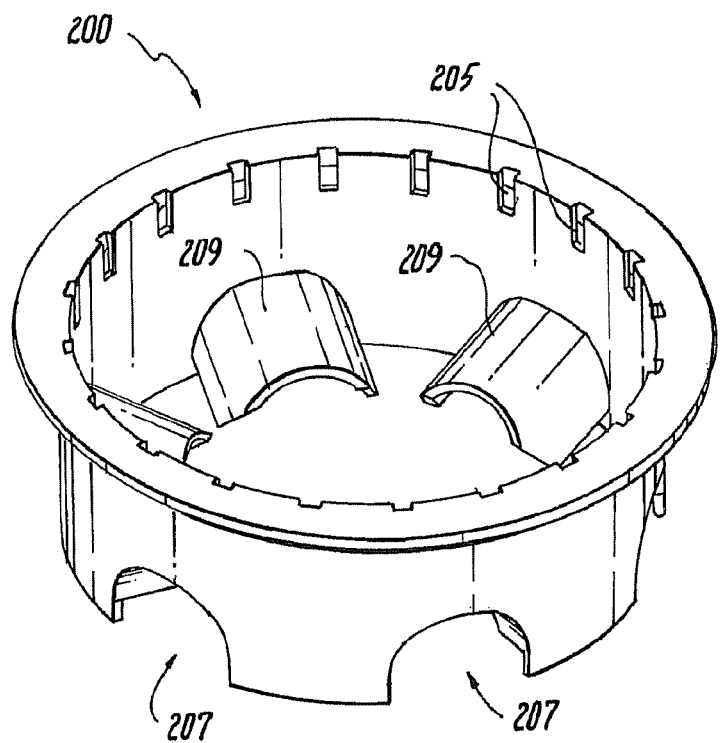
FIGS. 17-18 are isometric views of a suction extension section of the trocar of FIG. 1 in accordance with the disclosed embodiments.
Figure 18:
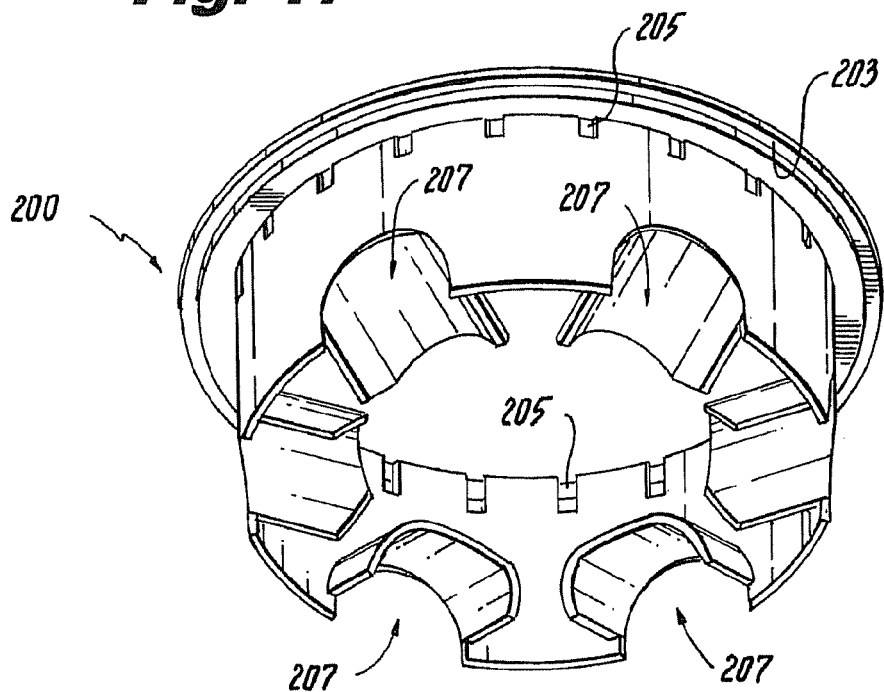
Figure 19:
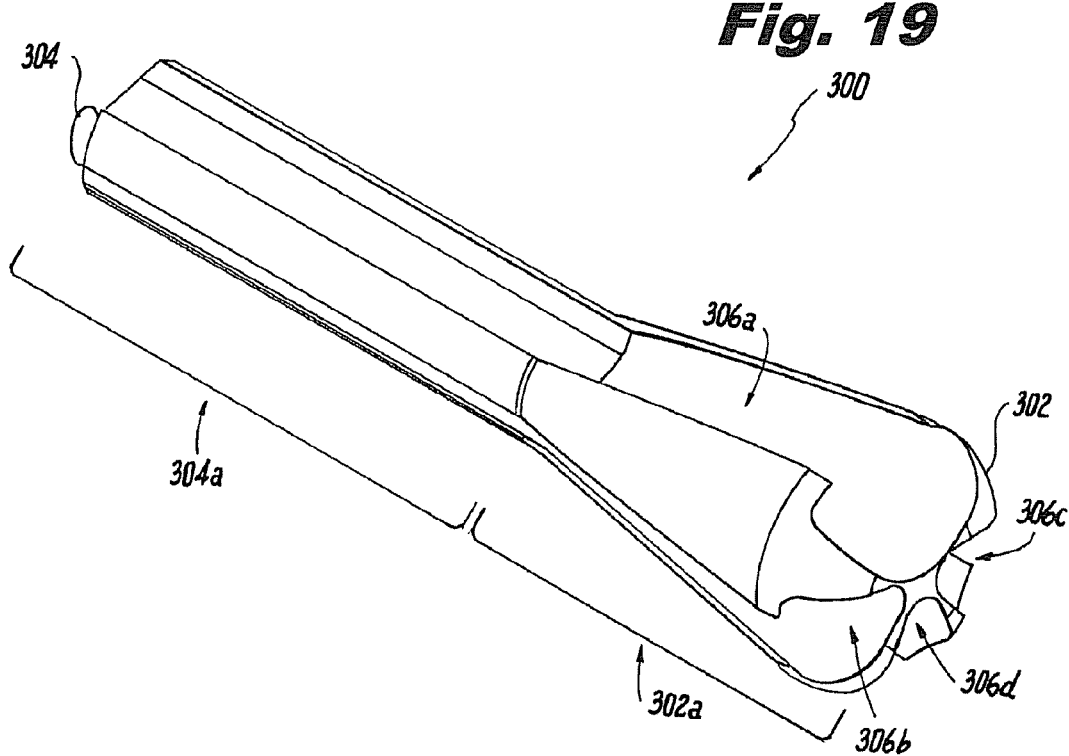
FIGS. 19-23 are various views of a first representative embodiment of an instrument guide in accordance with the disclosed embodiments.
Figure 20:
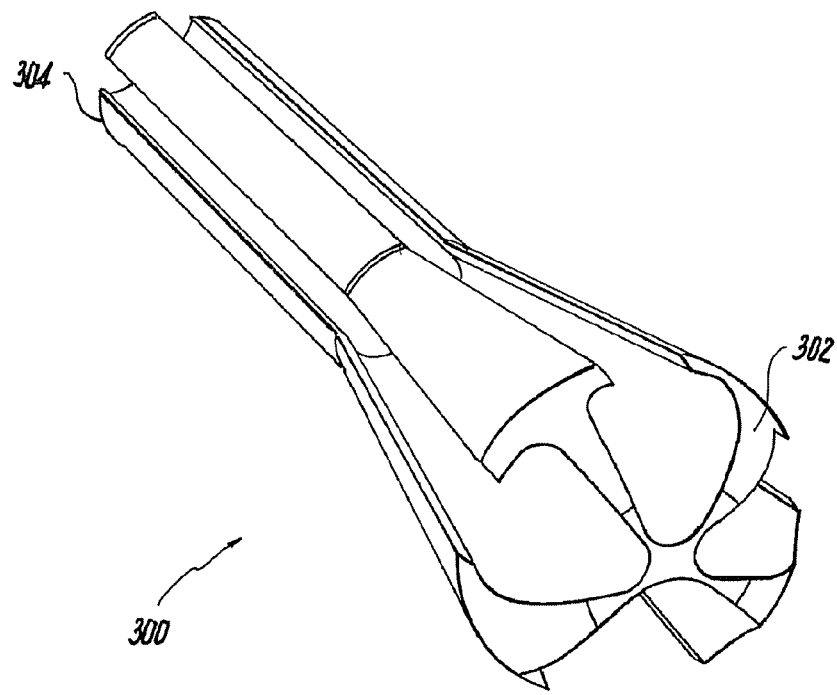

As illustrated, peripheral bead 162a of baffle 160 is held in place in a chamber 162b defined by cap spacer ring and spacer 140. Similarly, the periphery of distal portion 164 of baffle 160 is held in place between distal engagement surface 144 of spacer 140 and proximal engagement surface 172 of end cap 170. As illustrated, peripheral bead 164a of baffle 160 is held in place in a chamber 164b defined by spacer 140 and end cap 170. Annular engagement surface 174 of end cap is received by a proximal engagement surface 182 and inner circumferential surface 185 of tube center component 180 (FIGS. 14-15). Spacer 140, in turn, seats in the opening 156 of upper cap 150 defined by peripheral surface 152. Threads 154 on upper cap 150 mate with threads 111 on outer cannula 110. When assembled, screwing the cap 150 to the outer cannula 110 causes all nested components (110, 120, 180, 190, 200) to be firmly held together, providing for simple assembly of the trocar 100. Alternatively, the cap 150 can be secured to the outer cannula 110 in a different manner, including but not limited to other mechanical connections, such as latches, snaps, friction fit, adhesives, welding, such as heat or friction welding, including spin-welding, for example. Components 130, 140, 150, 160, 170 form a subassembly that can be removed, if desired, when inserting an instrument guide such as those depicted in FIGS. 19-28. Tabs 146 (FIG. 9) can facilitate removal of the subassembly. The subassembly is preferably left in place as the subassembly is very effective in reducing noise produced by trocar 100 when in operation. The components of the baffle subassembly are preferably welded or otherwise bonded together, clamping the baffle 160 in place. The subassembly preferably snaps into place to prevent unwanted movement with respect to the trocar in a proximal-distal direction, but permitting relative rotational movement. As such, a snap-in connection is preferred. Furthermore, leaving the baffle in place is also preferred because the material of baffle is generally suitable for gripping the instrument guide (300, 400) when inserted, preventing its removal. The instrument guide can also be provided with a snap fit to permit rotational movement of the guide with respect to trocar 100, but not undesired movement along a proximal-distal direction with respect to trocar 100.

For purposes of further illustration, and not limitation, tube center component 180 and ring jet assembly 190 nest to form one or more fluid jets. Specifically, as illustrated in FIG. 14, center component 180 defines one or more detents 183 on its outer surface. When the outer surface of center component 180 nests within the inner surface of ring jet assembly, the detent 183 cooperates with the inner surface of ring assembly to form a conduit that is in fluid communication with high pressure plenum 220 (FIG. 1). High pressure plenum 220 is pressurized with a working gas so as to drive a high speed gas flow through each of the jets disposed about the periphery of the distal circumferential interface 224 of the center component and the ring jet 190. A fluid tight seal about plenum 220 is ensured by seals 254, 256 disposed in circumferential grooves 181, 191 formed in each of center tube portion 180 and ring jet 190, respectively.

Preferably, the gas jets exit and wrap around the outer distal surface of the center tube component before breaking free of the surface, thus obtaining some angularity with respect to a longitudinal axis of the trocar, such that the main direction of the jet flow is generally off-axis, indicated for example by arrow "A" in FIG. 1. The momentum of the gas exiting the circumferentially disposed peripheral jets forms a pressure gradient inside the bore 106 of the trocar, such that the pressure at the distal end 102 of the trocar can be about 15 mm of Hg higher than the atmospheric pressure outside the trocar in the operating room. Proper axial spacing between center tube assembly 180 and ring jet 190 is ensured by the height of proximal spacers 192 disposed on the proximal face of the ring jet 190.

With further reference to FIG. 14, center tube assembly 180 further defines a plurality of recesses 187 about its distal periphery that are spaced to register with passages 207 defined in suction extension 200. Trocar 100 is preferably configured such that one aligned pair (187, 207) is aligned with ports (118, 128) in the outer cannula 110 and inner cannula 120 to facilitate passage of an instrument through external port 118 defined in outer cannula 110. Suction extension further defines a plurality of circumferentially disposed ports 205 about the proximal periphery thereof. Ports 205 provide for fluid communication between the annular space 260 (FIG. 1) defined between suction extension 200 and ring jet 190, and exhaust/recirculation plenum 230, such that gases and other fluids in annular space 260 can be evacuated from trocar 100. The arcuate awning-shaped members 209 that help define passages 207 are preferably arranged to register with recesses 187 and in between jets 183, as this arrangement has been found to result in more efficient flow dynamics. Although not depicted, the components of trocar 100 are preferably provided with molded in keys and slots to ensure consistent rotational alignment between different components thereof.

When assembled, the various components of trocar 100 described above cooperate to form a variety of passageways (106, 118/128/207) to receive the passage of surgical instruments as well as a plurality of fluid flow paths or plena (220, 230, 240). In operation, sensing plenum 240 includes one or more pressure sensors (not shown) in a fluid flow control unit (not shown) to maintain the pressure of a patient's abdomen at a preselected pressure (e.g., 15 mm Hg). Suitable gas flow control units are described, for example, in Provisional Patent Application Ser. No. 61/246,921, which is incorporated by reference herein in its entirety. For example, if the pressure detected in the abdomen is too high, the flow control unit decreases the delivery of gas to plenum 220, resulting in less gas being delivered through the high speed jets and into the bore 106 of the trocar 100. By way of further example, if the gas pressure is too low in the abdomen, the flow control unit increases the delivery of gas to plenum 220, resulting in more gas being delivered through the high speed jets and into the bore 106 of the trocar 100.

Having described operation of the exemplary trocar embodiment 100 above, use of the instrument guide will now be explained. For purposes of illustration, and not limitation, as embodied herein and as illustrated in FIGS. 19-24 and FIGS. 25-27, two exemplary instrument guides 300, 400 are provided.

Figure 21:
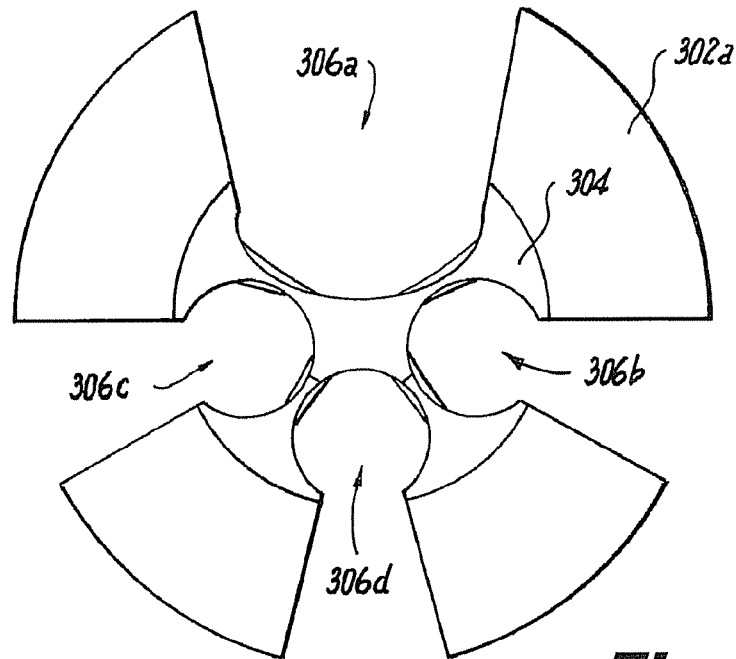
Figure 22:
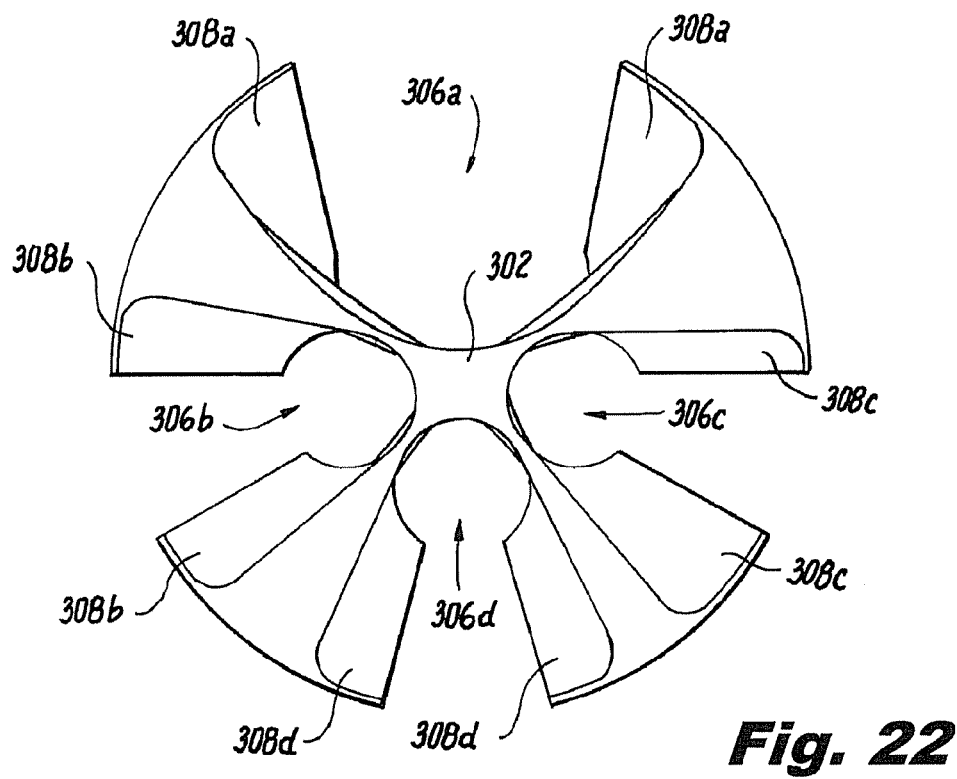
Figure 23:
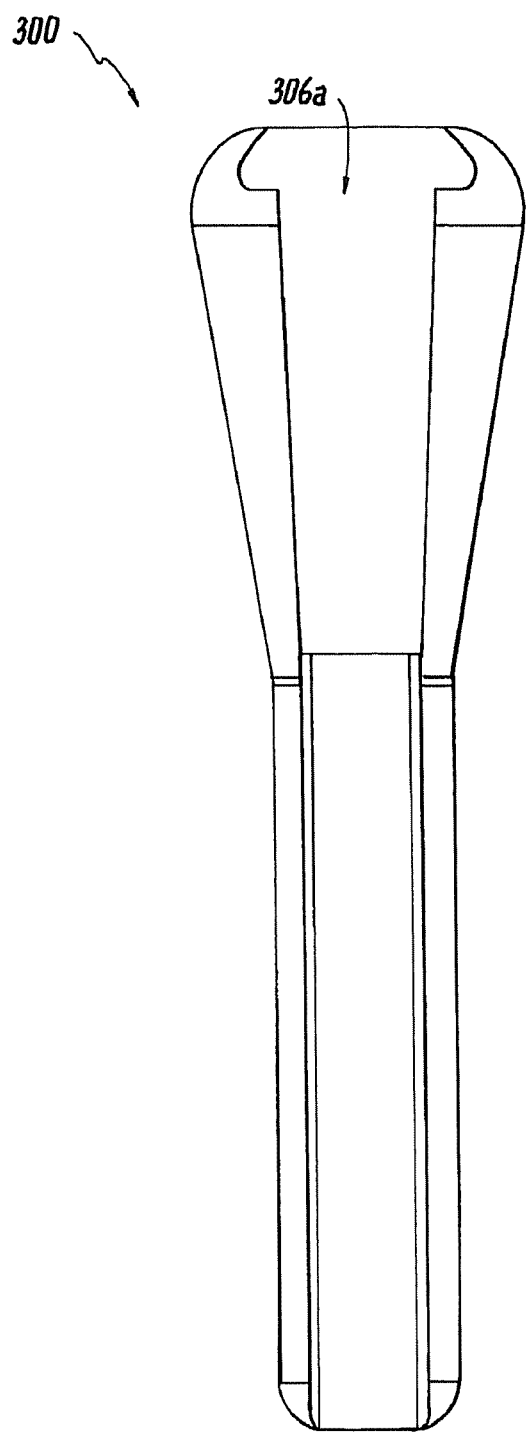

With reference to FIGS. 19-24, a first embodiment of an instrument guide 300 is depicted. Instrument guide has a proximal end 302, a radially-enlarged trumpet-shaped or flared proximal region 302a, a distal end 304 and an elongate distal region 304a. Instrument guide further includes a plurality of channels 306a-306d. FIG. 21 is a view of distal end 304 of instrument guide 300, whereas FIG. 22 is a view of proximal end 302 of instrument guide 300. FIG. 23 is a plan view of instrument guide with channel 306a at top. As depicted, channels 306b, 306c, 306d are generally round in cross-section in the distal region 304a of instrument guide 300, while channel 306a has a generally elliptical cross section in the distal region 304a of instrument guide 300. As illustrated in FIG. 22, angled channel walls 308 in each channel are provided.

Figure 24:
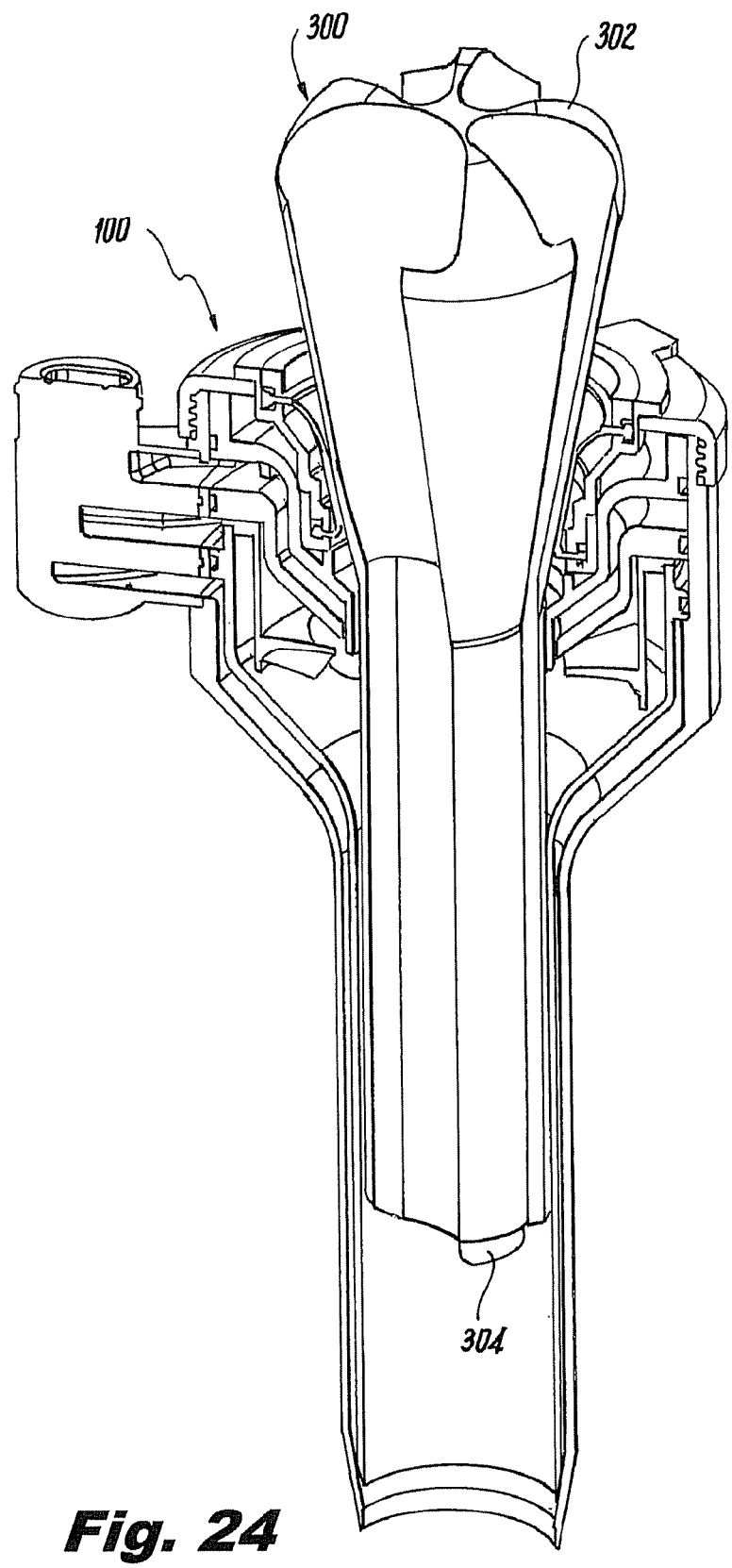
FIG. 24 is an isometric cut-away view of the trocar of FIG. 1 showing placement of the instrument guide of FIGS. 19-23.
Figure 27:
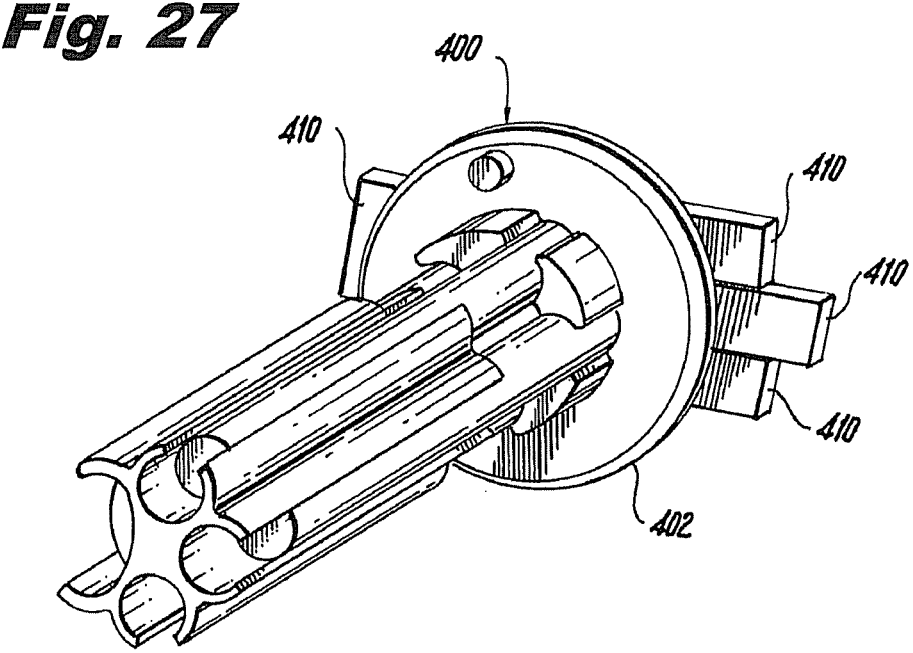
Figure 28:
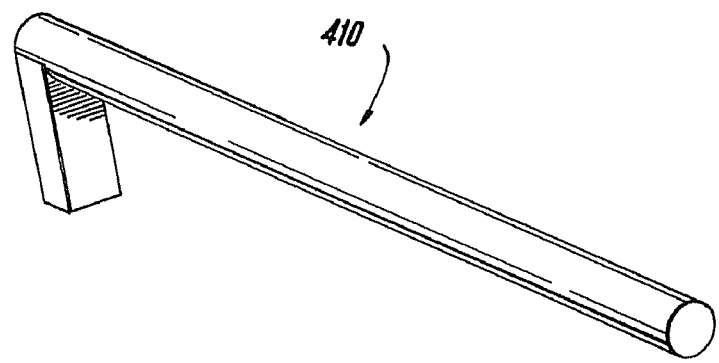

As illustrated in FIG. 24, in use, distal end 304 of instrument guide is introduced into bore of trocar 100. If desired, the subassembly including the baffle 160 may be removed. However, trocar 100 is illustrated in FIG. 24 without removing such subassembly. Instead, baffle 160, being made of a flexible material, is stretched out of the way. Once so inserted, instrument guide 300 provides fixed entry points for robotic surgical arms bearing instruments. The angled walls 308 of each channel 306 provide a larger opening to guide and facilitate alignment with each robotic arm as it approaches and enters each channel 306. Thus, if a robotic arm is introduced at an angle, the walls 308 of the channel 306 will guide the arm into the bore 106 of the trocar. A second embodiment of an instrument guide 400 is illustrated in FIGS. 25-27. Instrument guide 400 differs from instrument guide 300 principally in the respect that it does not include a trumpet-shaped proximal portion, but instead includes a proximal circumferential flange 402. A plurality of inserts 410 are illustrated in lieu of actual surgical instruments. One such insert is illustrated in detail in FIG. 28. All patents and patent applications referenced herein are incorporated by reference in their entireties for any purpose whatsoever.

The methods and systems of the present disclosure, as described above and shown in the drawings, provide for trocars and surgical systems with superior attributes as compared with systems of the prior art. It will be apparent to those skilled in the art that various modifications and variations can be made in the device and method of the present disclosure without departing from the spirit or scope of the disclosure. Thus, it is intended that the present disclosure include modifications and variations that are within the scope of the subject disclosure and equivalents.

What is claimed is:

1. A system for use in an automated surgical procedure, comprising:
a trocar having an outer cannula portion, an inner cannula portion within the outer cannula portion and defining a central lumen having a longitudinal axis, a ring jet assembly within the inner cannula portion and defining a nozzle for generating a gaseous seal within the central lumen of the inner cannula portion, the outer cannula portion having an outer side port formed therein and the inner cannula portion having an inner side port formed therein that is aligned with the outer side port of the outer cannula portion, the inner and outer side ports defining a channel having an axis oriented perpendicular to the longitudinal axis of the central lumen and being dimensioned and configured to receive a surgical instrument therethrough and into the central lumen of the inner cannula portion.

2. The system as recited in claim 1, further comprising an extension within the inner cannula portion below the ring jet assembly and including a plurality of circumferentially spaced part radially inwardly extending arcuate awnings each defining a passage, one such passage being aligned with the channel defined by the inner and outer side ports.

3. The system as recited in claim 2, wherein the nozzle includes a central tube portion axially aligned within the central lumen of the inner cannula portion and having a lower edge with a plurality of circumferentially spaced apart arcuate recesses formed therein for registering with the plurality of circumferentially spaced part radially inwardly extending arcuate awnings.

4. The system as recited in claim 1, further comprising an instrument guide having an elongated body dimensioned and configured for reception in the central lumen of the inner cannula portion, the body having a plurality of circumferentially spaced apart longitudinal channels, each configured to receive a surgical instrument.

5. The system as recited in claim 4, wherein each longitudinal channel is open along an outer periphery of the body of the instrument guide.

6. The system as recited in claim 4, wherein the instrument guide includes a radially-enlarged flared proximal region.

7. The system as recited in claim 4, wherein a proximal region of each of the channels of the instrument guide has radially outwardly diverging angled channel walls.

8. The system as recited in claim 4, wherein at least one of the channels of the instrument guide has a radially inner region with a generally circular cross-section.

9. The system as recited in claim 4, wherein at least one of the channels of the instrument guide has a radially inner region with a generally elliptical cross-section.

10. The system as recited in claim 4, further comprising a baffle nested above the ring jet assembly and held in place by a cap associated with the outer cannula portion.

11. The system as recited in claim 4, further comprising a baffle nested above the ring jet assembly and held in place by a cap associated with the outer cannula portion.

12. A system for use in an automated surgical procedure, comprising:
a) a trocar having an outer cannula portion, an inner cannula portion nested within the outer cannula portion and defining a central lumen having a longitudinal axis, the outer cannula portion having an outer side port formed therein and the inner cannula portion having an inner side port formed therein that is aligned with the outer side port of the outer cannula portion, the inner and outer side ports defining a channel having an axis oriented perpendicular to the longitudinal axis of the central lumen and being dimensioned and configured to receive a surgical instrument therethrough and into the central lumen of the inner cannula portion; and
b) an instrument guide having an elongated body dimensioned and configured for reception in the central lumen of the inner cannula portion of the trocar, the body having a plurality of circumferentially spaced apart longitudinal channels, each channel being configured to receive a surgical instrument extended into the central lumen as well as an auxiliary surgical instrument extended through the channel defined by the inner and outer side ports.

13. The system as recited in claim 12, further comprising a ring jet assembly within the inner cannula portion and defining a nozzle for generating a gaseous seal within the central lumen of the inner cannula portion.

14. The system as recited in claim 13, further comprising an extension within the inner cannula portion below the ring jet assembly and including a plurality of circumferentially spaced part radially inwardly extending arcuate awnings each defining a passage, one such passage being aligned with the inner and outer side ports.

15. The system as recited in claim 14, wherein the nozzle includes a central tube portion axially aligned within the central lumen of the inner cannula portion and having a lower edge with a plurality of circumferentially spaced apart arcuate recesses formed therein for registering with the plurality of circumferentially spaced part radially inwardly extending arcuate awnings.

16. The system as recited in claim 12, wherein each longitudinal channel is open along an outer periphery of the body of the instrument guide.

17. The system as recited in claim 12, wherein the instrument guide includes a radially-enlarged flared proximal region.

18. The system as recited in claim 12, wherein a proximal region of each of the channels of the instrument guide has radially outwardly diverging angled channel walls.

19. The system as recited in claim 12, wherein at least one of the channels of the instrument guide has a radially inner region with a generally circular cross-section.

20. The system as recited in claim 12, wherein at least one of the channels of the instrument guide has a radially inner region with a generally elliptical cross-section.

* * * * *